United States Patent [19]

Lechtken et al.

[11] Patent Number: 4,621,109
[45] Date of Patent: Nov. 4, 1986

[54] POLYPROPYLENE STABILIZING ANTI-OXIDANT 2,3-DIHYDROBENZ-4-OXA-1-THIIN DERIVATIVES, COMPOSITIONS AND METHOD OF USE THEREFOR

[75] Inventors: Peter Lechtken, Frankenthal; Hübert Traüth, Dudenhofen; Stefan Weiss, Neckargemuend; Albert Hettche, Hessheim, all of Fed. Rep. of Germany

[73] Assignee: BASF Aktiengesellschaft, Ludwigshafen, Fed. Rep. of Germany

[21] Appl. No.: 743,682

[22] Filed: Jun. 11, 1985

[30] Foreign Application Priority Data

Jun. 14, 1984 [DE] Fed. Rep. of Germany ....... 3421977

[51] Int. Cl.$^4$ .................... C07D 327/06; C08K 5/46; C08K 5/9
[52] U.S. Cl. ........................... 524/83; 549/15; 549/16; 426/269
[58] Field of Search ............... 549/15, 16; 524/83

[56] References Cited
FOREIGN PATENT DOCUMENTS 0731495 6/1955 United Kingdom ............... 549/16

OTHER PUBLICATIONS

Thomae, abstract of Br. Pat. No. 1,167,851, Derwent vol. 4, No. 20, Germain 16. 4.64, p. 4.

*Primary Examiner*—Henry R. Jiles
*Assistant Examiner*—J. G. Mullins
*Attorney, Agent, or Firm*—Keil & Weinkauf

[57] ABSTRACT 2,3-Dihydrobenz-4-oxa-1-thiins of the general formula I

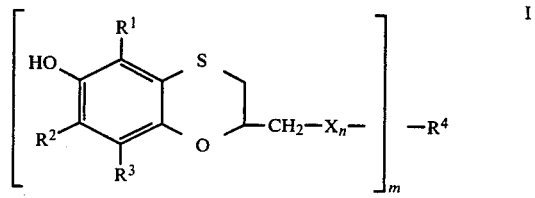

where $R^1$, $R^2$ and $R^3$ are each hydrogen, methyl or methoxy, and $R^2$ and $R^3$ together may furthermore be a fused benzene ring, $R^4$ is hydrogen or an m-valent aliphatic hydrocarbon radical which may be interrupted by sulfur and/or carry thiol groups as substituents, or is halogen when n is zero, X is —O—, —S— or —O—CO—, m is 1 or 2 and n is zero or 1, are useful as antioxidants for organic materials.

4 Claims, No Drawings

POLYPROPYLENE STABILIZING ANTI-OXIDANT 2,3-DIHYDROBENZ-4-OXA-1-THIIN DERIVATIVES, COMPOSITIONS AND METHOD OF USE THEREFOR

The present invention relates to 2,3-dihydrobenz-4-oxa-1-thiins of the general formula I

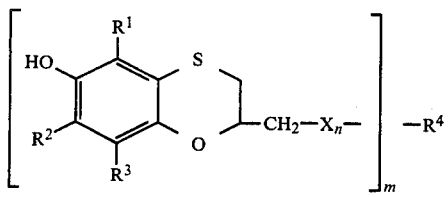

where $R^1$, $R^2$ and $R^3$ are each hydrogen, methyl or methoxy, and $R^2$ and $R^3$ together may furthermore be a fused benzene ring, $R^4$ is hydrogen or an m-valent aliphatic hydrocarbon radical which may be interrupted by sulfur and/or carry thiol groups as substituents, or is halogen when n is zero, X is —O—, —S— or —O—CO—, m is 1 or 2 and n is zero or 1.

The present invention furthermore relates to the preparation of the compounds of the formula I and their use as antioxidants for organic materials, and to organic materials which contain the compounds I.

Compounds of the type I'

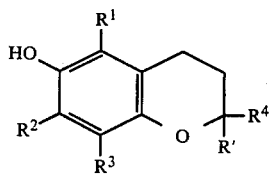

R=H, organic radical ie. those which contain the structural unit of the chroman

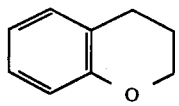

are well known antioxidants. For example, alphatocopherol (vitamin E) is derived from chroman, and various chroman derivatives are described in, inter alia, European Laid-Open Application Nos. 0,036,160, 0,036,169 and 0,057,427.

It is an object of the present invention to provide industry with antioxidants which are even more effective than the chroman derivatives I known to date.

We have found that this object is achieved by the dihydrobenzoxathiins defined at the outset.

The novel compounds I differ from the known chroman derivatives in principle only in that they have a sulfur atom instead of a —CH$_2$— group in the 4-position of the chroman skeleton; surprisingly, however, their activity as antioxidants is superior to that of the corresponinng chroman compounds.

The compounds I are obtainable by conventional methods, in which the essential synthesis step is the condensation of a quinone II

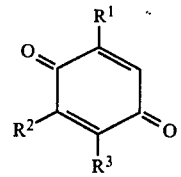

with a thioglycol III

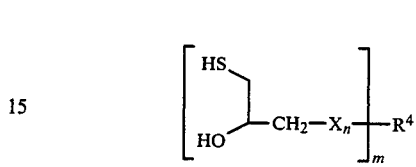

in which cyclization takes place.

This condensation reaction involving cyclization takes place readily at 40°–150° C., preferably 50°–110° C., preferably in the presence of an acid, with simultaneous elimination of water. Particularly suitable acids are mineral acids, such as hydrochloric acid and phosphoric acid, their concentration advantageously being such that the reaction mixture has a pH of less than 1.

In general, it is preferable to carry out the reaction of II with III in the presence of a solvent or diluent, water being preferred. Other suitable solvents are water-soluble solvents such as alcohols, tetrahydrofuran and dioxane, as well as mixtures of these with water. Water-immiscible solvents, such as toluene, petroleum ether and chlorobenzene, may also be used.

Those compounds I in which $R^4$ is one of the hydrocarbon radicals conforming to the definition can be synthesized by the above procedure by first preparing one of the other compounds I in which m is 1, ie. a compound containing the side chain group —CH$_2$—OH, —CH$_2$—SH or —CH$_2$—Hal (where Hal is halogen, in particular Cl or Br), and then reacting the compound obtained, in a conventional manner, with a compound IV

where Y is a functional group capable of linking the hydrocarbon radical $R^4$ to the group —CH$_2$—X$_n$— in conformity with the definition.

If it is intended to prepare, for example, compounds I containing an ether or thioether group, a compound I possessing a side chain group (—CH$_2$—OH) or (—CH$_2$—SH) is reacted with, for example, a halogen compound IV (where Y is halogen) or an olefinic compound IV (where Y is CH$_2$=CH—), or, conversely, a compound I containing the side chain group —CH$_2$—Hal is reacted with an alcohol or thiol IV (where Y is HO— and HS—, respectively).

Compounds I containing the ester group —CH$_2$—O—CO— can be prepared, for example, by esterification or transesterification (Y=|—COOH|, |—CO Hal|, |—CO—O—CH$_3$|).

If the coupling reactions take place with elimination of acids, eg. a hydrohalic acid, it is advisable to bind these by means of a base, such as sodium hydroxide solution, pyridine or trimethylamine. If the reaction is one of the other reactions, such as addition at an olefinic group or the esterification of an alcohol with an acid, the presence of a strong acid, such as p-toluenesulfonic acid, or of an acidic ion exchanger is advantageous.

In other respects, the stated coupling reactions are standard operations in preparative chemistry, so that further description can be dispensed with here.

If the group ($-X_n-R^4$) is halogen, it is also possible to halogenate the corresponding hydroxy compound.

Starting compounds II are known, or are obtainable in a conventional manner (cf., for example, Houben-Weyl, Methoden der Organischen Chemie, 4th edition, volume 7/3a, pages 23-112). The same applies in the case of the thioglycols III (Houben-Weyl, 4th edition, volume 9, pages 22-23) and the monofunctional and bifunctional compounds IV.

Since the compounds I are by their very nature sensitive to oxidation, it is advantageous to carry out all operations under a protective gas atmosphere, for example under nitrogen.

Preferred compounds I are those in which $R^1$, $R^2$ and $R^3$ are each methyl, $R^4$ is an aliphatic $C_2$-$C_{18}$-hydrocarbon radical and n is 1. It has furthermore been found that sulfur, in the form of a thioether or thiol functional group, reinforces the antioxidative effect; hence, preferred radicals $R^4$ are the sulfur-containing hydrocarbons conforming to the definition. Examples of such radicals are $-CH_2-SH$, $-CH_2CH_2-S-CH_2CH_3$ and $-CH(SH)-CH_3$.

The novel compounds I are very useful as antioxidants for stabilizing organic materials to oxidation and thermal oxidation. Examples of such materials are plastics, foodstuffs, animal feeds and particularly sensitive substances such as dyes, vitamins, unsaturated fats and pharmaceutical, veterinary and cosmetic active ingredients and formulations.

The concentration of I in the organic materials is in general from 0.005 to 50% by weight. In the case of plastics, foodstuffs and animal feeds, concentrations from 0.005 to 1% by weight are usually sufficient. In contrast, the concentrations in the case of vitamins and similar highly sensitive substances may be up to 50% by weight.

In the case of plastics, especially polypropylene, the compounds I substantially increase not only the resistance to aging but also the stability to processing.

We have furthermore found that the antioxidative effect of the compounds I is reinforced by aliphatic and cycloaliphatic polyols, which act as synergistic agents. Examples of such polyols, which should contain not less than 2, preferably 3-6, free alcoholic hydroxyl groups in the molecule, are ethylene glycol, glycerol, trimethylolpropane and in particular sugars and hydrogenated sugars, such as sorbitol. Some of the hydroxyl groups of the polyols may furthermore be etherified with alkanols or esterified with fatty acids.

The concentration of the polyols in the organic materials is from 0.005 to 90% by weight, and the sum of the concentrations of I and the polyols may be as high as 99% by weight. In the case of less sensitive materials, such as plastics, foodstuffs and animal feeds, the concentration of I is about 0.001-0.3% by weight, and the ratio of the concentration of I to that of the polyols is preferably from 1:1 to 1:10.

The compounds I also provide further possible methods for synthesizing tocopherol-like substances.

EXAMPLES

Below, the radical

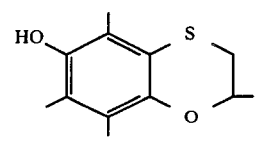

is referred to as radical A, and the radical

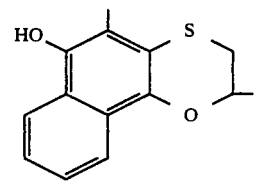

is referred to as radical B.

EXAMPLE 1

Preparation of A—CH$_2$—OH 150 g (1.0 mole) of molten trimethylquinone was added to a solution of 151 g (1.4 moles) of propane-1,2-diol-3-thiol, 1 l of water and 25 ml of concentrated hydrochloric acid under a nitrogen atmosphere at 50° C., and the mixture was heated at the boil for 2.5 hours. When the mixture was subsequently cooled, the above compound was obtained in the form of pale beige crystals.

The crystals were separated off, washed with warm water and cold water, dried over calcium chloride and recrystallized from 500 ml of acetonitrile to give 177 g of product. A further 46 g of the product were obtained from the mother liquor, so that the total yield was 92%. Mp. 118°-120° C.

EXAMPLE 2

Preparation of A—CH$_2$—Br 48 g (0.2 mole) of the product of Example 1 were added a little at a time to a brominating reagent prepared from 55 g (0.21 mole) of triphenylphosphine, 1 of dry methylene chloride and 34 g (0.212 mole) of bromine. The dark brown solution was heated at the boil (about 40° C.) for 3 hours and then stirred into 1 L of a 5% strength by weight sodium bicarbonate solution.

Thereafter, the organic phase was separated off, washed with dilute NaCl solution, dried with Na$_2$SO$_4$ and evaporated down under reduced pressure in a rotary evaporator. The residue was taken up with 250 ml of diethyl ether, triphenylphosphine oxide separating out. The remaining organic phase was evaporated down, the residue was taken up with 200 ml of a mixture of 3 parts by volume of cyclohexane and 1 part by volume of ethyl acetate, and the solution was filtered over silica gel and eluted with about 2 L of the same solvent. Evaporation of the filtrate gave the above bromine compound in the form of brownish crystals, which had a melting point of 87°-88° C. after extraction by boiling with petroleum ether. Yield: 75%.

EXAMPLE 3

Preparation of B—CH$_3$—OH 34.4 g (0.2 mole) of powdered 2-methyl-1,4-naphthoquinone were added a little at a time to a solution of 30.2 g (0.28 mole) of propane-1,2-diol-3-thiol, 200 ml of water and 5 ml of concentrated hydrochloric acid at 50° C. under a nitrogen atmosphere, and the mixture was heated at the boil for 2 hours. Thereafter, the aqueous phase was separated off at 70° C. and the remaining melt was washed twice with the same volume of water, at this temperature. The subsequent suspension in cold water gave the product as a pale gray crystalline mass, which was separated off, dried over $CaCl_2$ and then recrystallized from 200 ml of acetonitrile to give pale gray to colorless crystals of melting point 142°–144° C. Yield: about 70%.

EXAMPLE 4

Preparation of A—CH₃

This compound was prepared in 60% yield from trimethylquinone and propan-2-ol-1-thiol in the manner described in Example 1. Mp. 86°–87° C.

EXAMPLE 5

Preparation of (A—CH₂—O—CO—CH₂—CH₂—)₂S 24 g (0.1 mole) of the product from Example 1 were heated together with 8.9 g (0.05 mole) of thiodipropionic acid and 0.5 g of p-toluenesulfonic acid in 50 ml of toluene under a nitrogen atmosphere, the water being separated off. After 3 to 4 hours, the mixture was cooled, and some of the product was precipitated. The mixture was brought into solution again with methylene chloride, and the solution was extracted by shaking with dilute $NaHCO_3$ solution, washed with water, dried, treated with 2 g of active carbon and evaporated down under reduced pressure in a rotary evaporator. The residue was recrystallized from about 50 ml of isopropanol. Yield: 62%; mp. 81°–83° C.

EXAMPLE 6

Preparation of A—CH₂—O—CO—CH₂—SH, 24 g (0.1 mole) of the product from Example 1 were heated together with 10.1 g (0.11 mole) of thioglycolic acid and 0.5 g of p-toluenesulfonic acid in 50 ml of toluene under a nitrogen atmosphere, with removal of the water. When the reaction mixture was worked up in a conventional manner, the above compound was obtained in the form of a pale brown oil, in a yield of 95%.

EXAMPLE 7

Preparation of A—CH₂—O—CO—C₁₇H₃₅

This compound was prepared in a yield of 61% from the compound A—CH₂—OH and stearic acid by a method similar to that desired in Example 6. Mp. 69°–71° C.

EXAMPLE 8

Preparation of B—CH₂—O—CO—C₁₇H₃₅

This compound was prepared in a yield of 77% from the compound B—CH₂—OH and stearic acid by a method similar to that described in Example 3, beige crystals of melting point 54°–56° C. being obtained.

EXAMPLE 9

Stabilizing effect of various antioxidants in lard

Lard containing in each case 0.02% by weight of various antioxidants was subjected to the peroxide test (Oil and Soap, 15 (1938), 184). In this test, the samples were stored in the presence of air at 80° C. until the peroxide number (PON) reached 50. The longer this time t, the more effective is the antioxidant.

The test results, which speak for themselves, are shown in Table 1.

TABLE 1

| Peroxide test for Lard according to Example 9 | | | |
|---|---|---|---|
| Test | Antioxidant | According to Example | t [days] |
| For comparison | | | |
| 1 V | alpha-tocopherol | — | 1 |
| 2 V | 2,5,7,8-tetramethyl-2-(2-hydroxyeth-1-yl)-5-hydroxychroman | — | 5 |
| 3 V | as for 2 V, but esterified in the side chain with stearic acid | — | 4 |
| According to the invention | | | |
| 1 | A—CH₂—OH | 1 | 7 |
| 2 | B—CH₂—OH | 3 | 12 |
| 3 | (A—CH₂—O—CO—CH₂CH₂)₂ | 5 | 13 |
| 4 | A—CH₂—O—CO—CH₂—SH | 6 | 10 |
| 5 | B—CH₂—O—CO—C₁₇H₃₅ | 8 | 9 |

EXAMPLE 10

Stabilizing effect of various antioxidants in dry canthaxanthin powder

Canthaxanthin, which is used as an additive in feeds for layers, was mixed with 4% by weight of the antioxidant A—CH₂—O—CO—C₁₇H₃₅ according to Example 7, and the mixture was processed in a conventional manner with gelatine to give a dry powder. This powder was then mixed with a commercial feed for layers so that the concentration of active ingredient was 200 ppm. After storage for 8 weeks at 40° C. and 70% relative humidity, the residual canthaxanthin content was 66% of the initial concentration.

In a comparative test without the addition of an antioxidant, no canthaxanthin was detectable. When the antioxidant according to test 3 V in Table 1 was used, the residual content of active ingredient was only 43%.

EXAMPLE 11

Stabilization of polypropylene to processing

Pure polypropylene powder having a mean molecular weight of 10,000 was mixed, in each case, with 0.1% by weight of an antioxidant or of a mixture of various antioxidants, and the mixture was extruded at 250° C. and then converted to granules. Extrusion and granulation were repeated several times, the melt flow index MFI of the particular granular sample being measured at 190° C. in accordance with DIN 53,135 after the 1st, 3rd, 5th and 8th passes. The higher the melt index, the greater is the degradation of the polypropylene as a result of the thermal load during extrusion, and the lower is the stability to processing.

The color of the material after the 8th extrusion pass was also determined.

The results of the tests are shown in Table 2.

EXAMPLE 12

Stabilization of polypropylene: long-term stability

The material described in Example 11 was subjected to oven aging according to DIN 53,383 and then processed first to granules at 220° C. and then to 20×20×1 mm³ panels at 220° C. The panels were stored at 140° C. in a through-circulation oven with a supply of fresh air.

In this test, the panels became brittle, and the time t taken in each case to reach a certain degree of embrittlement, identical for all tests, was determined. This time is not only a direct measure of oven aging but also an indirect measure of the long-term stability.

The results of these tests are likewise shown in Table 2.

TABLE 2

Stabilization of polypropylene according to Examples 11 and 12

| Test No. | Antioxidant according to Example | Synergistic agent | $q^1$ | Color$^2$ | MFI after passes 1 | 3 | 5 | 8 | Oven aging t \|h\| |
|---|---|---|---|---|---|---|---|---|---|
| For comparison | | | | | | | | | |
| 1 V | — | sorbitol | — | 0 | 7 | 13 | 20 | 30 | 2 |
| 2 V | see 3 V from Table 1 | — | 0 | 3 | 4 | 6 | 7 | 8 | 200 |
| 3 V | " | sorbitol | 2 | 3 | 4 | 5 | 6 | 7 | 200 |
| 4 V | " | " | 4 | 2 | 5 | 6 | 9 | 11 | 150 |
| According to the invention | | | | | | | | | |
| 1 | Example 7 | — | 0 | 3 | 5 | 6 | 8 | 10 | 400 |
| 2 | " | sorbitol | 2 | 3 | 5 | 6 | 7 | 9 | 290 |
| 3 | " | " | 4 | 2 | 5 | 5 | 6 | 7 | 200 |
| 4 | " | " | 6 | 2 | 5 | 6 | 7 | 10 | —$^3$ |

$^1$ratio of synergistic agent to antioxidant
$^2$between 0 (colorless) and 6 (brown)
$^3$not measured

We claim:

1. A 2,3-dihydrobenz-4-oxa-1-thiin of the formula I

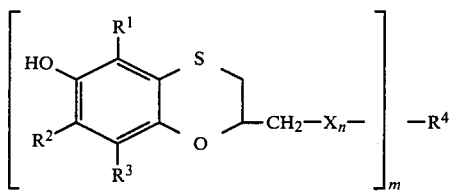

where $R^1$, $R^2$ and $R^3$ are each hydrogen, methyl or methoxy, and $R^2$ and $R^3$ together may furthermore be a fused benzene ring, $R^4$ is hydrogen or an m-valent aliphatic $C_2$-$C_{18}$-hydrocarbon radical which may be interrupted by sulfur and/or carry thiol groups as substituents, or is halogen when n is zero, X is —O—, —S— or —O—CO—, m is 1 or 2 and n is zero or 1.

2. An polypropylene material which is sensitive to oxidation, as defined in claim 1, which additionally contains from 0.005 to 90% by weight of an aliphatic and/or cycloaliphatic polyol.

3. A method of stabilizing polypropylene materials that are sensitive to oxidation which comprises, adding to the oxygen-sensitive material an effective amount of a compound of formula I as defined in claim 1.

4. A stabilized composition which comprises an oxygen-sensitive polypropylene material and from 0.005 to 50% by weight based on the weight of the organic material of a compound of formula I as defined in claim 1.

* * * * *